United States Patent [19]

Lesher et al.

[11] Patent Number: 4,463,008

[45] Date of Patent: Jul. 31, 1984

[54] 2-ALKOXY-5-(PYRIDINYL)PYRIDINES AND CARDIOTONIC USE THEREOF

[75] Inventors: George Y. Lesher; Chester J. Opalka, Jr., both of Schodack; Baldev Singh, East Greenbush, all of N.Y.

[73] Assignee: Sterling Drug Inc., New York, N.Y.

[21] Appl. No.: 440,505

[22] Filed: Nov. 10, 1982

[51] Int. Cl.$^3$ .................... A61K 31/44; C07D 401/04
[52] U.S. Cl. .................... 424/263; 424/266; 546/257; 546/258
[58] Field of Search .............. 546/257, 258; 424/263, 424/266

[56] References Cited

U.S. PATENT DOCUMENTS

| | | |
|---|---|---|
| 3,655,679 | 4/1972 | Shen et al. |
| 4,107,315 | 8/1978 | Lesher et al. ............ 546/257 |
| 4,137,233 | 1/1979 | Lesher et al. ............ 546/257 |
| 4,225,601 | 9/1980 | Lesher et al. ............ 546/258 |
| 4,225,715 | 9/1980 | Lesher et al. ............ 546/257 |
| 4,312,875 | 1/1982 | Lesher et al. |
| 4,313,951 | 2/1982 | Lesher et al. ............ 546/258 |
| 4,347,363 | 8/1982 | Singh . |

OTHER PUBLICATIONS

Baker et al., [Drug Metab. Dispos., vol. 10, No. 2, pp. 168–172, (1982)].
P. Nantka-Namirski et al., [Pol. J. Pharmacol. Pharm. 30, No. 5, pp. 707–712, (1978)].

*Primary Examiner*—Jane T. Fan
*Attorney, Agent, or Firm*—Robert K. Bair; B. Woodrow Wyatt; Paul E. Dupont

[57] ABSTRACT

2-($R_1$O)-3-Q-5-PY-6-R-pyridine (I) or pharmaceutically acceptable acid-addition salts thereof are useful cardiotonics, where $R_1$ is methyl or ethyl, R is hydrogen or lower-alkyl, PY is 4(or 3)-pyridinyl or 4(or 3)-pyridinyl having one or two lower-alkyl substituents, and Q is hydrogen, chloro or COOR' where R' is lower-alkyl, or Q is cyano only when R is hydrogen. The preparation of I and their cardiotonic use are shown.

9 Claims, No Drawings

2-ALKOXY-5-(PYRIDINYL)PYRIDINES AND CARDIOTONIC USE THEREOF

BACKGROUND OF THE INVENTION (a) Field of the Invention

This invention relates to 2-alkoxy-5-(pyridinyl)pyridines and cardiotonic use thereof.

(b) Description of the Prior Art

Baker et al. [Drug Metab. Dispos., Vol. 10, No. 2, pp. 168–172 (1982)] show, inter. alia, 6-methoxy-(3,4'-bipyridin)-5-amine, alternatively named 3-amino-2-methoxy-5-(4-pyridinyl)pyridine.

P. Nantka-Namirski et al. [Pol. J. Pharmacol. Pharm. 30, No. 5, pp. 707–712 (1978)] in a paper entitled "Cancerostatics III. Synthesis and Some Chemical Transformations of 3-cyano-5-(pyridyl-4-)pyrid-2-one" show, inter alia, the reaction of 3-dimethylamino-2-(4-pyridinyl)acrolein with malononitrile and sodium methoxide in methanol at room temperature to produce 3-cyano-2-methoxy-5-(4-pyridinyl)pyridine. Also shown in this paper is 2-chloro-3-cyano-5-(4-pyridinyl)pyridine, disclosed in the instant application as an intermediate to prepare 3-cyano-2-methoxy-5-(4-pyridinyl)pyridine.

Singh [U.S. Pat. No. 4,347,363, issued Aug. 31, 1982] shows the reaction of pyridinylmethyl lower-alkyl ketone with ethoxymethylenemalononitrile in a lower-alkanol, e.g., ethanol, to produce 1,2-dihydro-6-methyl-2-oxo-5-(pyridinyl)nicotinonitrile, alternatively named 3-cyano-6-methyl-5-(pyridinyl)-2(1H)-pyridinone.

Shen et al. [U.S. Pat. No. 3,655,679, issued Apr. 11, 1972] show, inter alia, the reaction of 2-arylacetoacetaldehyde with ethyl cyanoacetate in methanol in the presence of piperidine to produce methyl 5-aryl-2-hydroxy-6-methylnicotinate, where aryl is phenyl or substituted-phenyl.

Lesher, Opalka and Page [U.S. Pat. No. 4,312,875, issued Jan. 26, 1982] show, inter alia, as cardiotonic agents 5-(pyridinyl-6-(lower-alkyl)-2(1H)-pyridinones and corresponding lower-alkyl 1,2-dihydro-5-(pyridinyl)-2-oxo-6-(lower-alkyl)nicotinates.

SUMMARY OF THE INVENTION

In a composition of matter aspect, the invention resides in 2-($R_1$O)-3-Q-5-PY-6-R-pyridine (I), or salts thereof, useful as cardiotonic agents, where $R_1$, Q, PY and R are defined hereinbelow.

A composition aspect of the invention resides in the cardiotonic composition for increasing cardiac contractility, said composition comprising a pharmaceutically acceptable carrier, and as the active component thereof, a cardiotonically effective amount of 2-($R_1$O)-3-Q-5-PY-6-R-pyridine (I) or salts thereof.

A method aspect of the invention resides in the method for increasing cardiac contractility in a patient requiring such treatment which comprises administering to said patient a medicament comprising a pharmaceutically acceptable carrier and, as the active component, a cardiotonically effective amount of 2-($R_1$O)-3-Q-5-PY-6-R-pyridine (I), where Q has the definition given hereinbelow and also where Q is cyano when R is hydrogen.

DETAILED DESCRIPTION INCLUSIVE OF PREFERRED EMBODIMENTS

A composition of matter aspect of the invention resides in a 2-($R_1$O)-3-Q-5-PY-6-R-pyridine having formula I

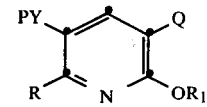

or an acid-addition salt thereof, where $R_1$ is methyl or ethyl, R is hydrogen or lower-alkyl, Q is hydrogen, bromo, chloro or COOR' where R' is lower-alkyl, and PY is 4(or 3)-pyridinyl or 4(or 3)-pyridinyl having one or two lower-alkyl substituents. The compounds of formula I are useful as cardiotonics, as determined by standard pharmacological evaluation procedures. Preferred embodiments are those of formula I where $R_1$ is methyl, Q is hydrogen, PY is 4(or 3)-pyridinyl and R is methyl or ethyl. A particularly preferred embodiment is 2-methoxy-6-methyl-5-(4-pyridinyl)pyridine or said salts thereof.

A composition aspect of the invention resides in a cardiotonic composition for increasing cardiac contractility, said composition comprising a pharmaceutically acceptable carrier and, as the active component thereof, a cardiotonically effective amount of the compound of formula I where $R_1$, R, Q and PY have the above-given meaning. Preferred embodiments of this composition aspect of the invention are those where the active component is the compound of formula I where $R_1$ is methyl, Q is hydrogen, PY is 4(or 3)-pyridinyl and R is methyl or ethyl. A particularly preferred embodiment is the composition where the active component is 2-methoxy-6-methyl-5-(4-pyridinyl)pyridine or said salts thereof.

A method aspect of the invention resides in the method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of the compound of formula I or pharmaceutically acceptable acid-addition salt thereof, where $R_1$ is methyl or ethyl, R is hydrogen a lower-alkyl, PY is 4(or 3)-pyridinyl or 4(or 3)-pyridinyl having one or two lower-alkyl substituents and Q is hydrogen, bromo, chloro or COOR' where R' is lower-alkyl or Q is cyano only when R is hydrogen. Preferred and particularly preferred embodiments of this method aspect of the invention are those where the active component is the same as the active component of the respective preferred and particularly preferred composition embodiments described in the immediately preceding paragraph.

The term "lower-alkyl" as used herein, e.g., as one of the meanings for R or R' or as a substituent for PY in formula I means alkyl radicals having from one to four carbon atoms which can be arranged as straight or branched chains, illustrated by methyl, ethyl, n-propyl, isopropyl, n-butyl, sec.-butyl, tert.-butyl and isobutyl.

Illustrative of PY in formula I where PY is 4-pyridinyl having one or two lower-alkyl substituents are the following: 2-methyl-4-pyridinyl, 2,6-dimethyl-4-pyridinyl, 3-methyl-4-pyridinyl, 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diisopropyl-4-pyridinyl, and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form; however, appropriate pharmaceutically acceptable salts within the scope of the invention are those derived from mineral acids such as hydrochloric acid, hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, acetate, citrate, lactate, tartrate, methanesulfonate, ethanesulfonate, benzenesulfonate, cyclohexylsulfamate and quinate respectively.

The acid-addition salts of said basic compounds (I) are prepared either by dissolving the free base in anhydrous alcohol solution or in other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds of formula I are preferred, all acid-addition salts are within the scope of the invention. All acid-addition salts are useful as sources of the free base form even if the particular salt per se is desired as an intermediate product as for example when the salt is formed only for purposes of purification or identification, or when it is used as an intermediate in preparing a pharmaceutically acceptable salt by ion exchange procedures.

The molecular structures of the compounds of formula I were assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same.

The compounds of formula I where Q is hydrogen, bromo, chloro or cyano are prepared by heating the corresponding 2-bromo(or chloro)-3-Q-5-PY-6-R-pyridine with an alkali metal methoxide or ethoxide, preferably sodium or potassium methoxide or ethoxide, to prepare the corresponding 2-methoxy(or ethoxy)-3-Q-5-PY-6-R-pyridine. The intermediate 2-bromo(or chloro)-3-Q-5-PY-6-R-pyridines are disclosed as intermediates and claimed in Lesher et al. U.S. Pat. Nos. 4,297,360 and 4,351,941, issued Oct. 27, 1981 and Sept. 28, 1982 respectively.

The compounds of formula I where Q is COOR' and R is lower-alkyl are prepared by heating a ketone of the formula, PY—CH$_2$—C(=O)—R with a lower-alkyl α-cyano-β-(R"O)-2-propenoate of the formula R"OCH=C(CN)—COOR' where R" is preferably ethyl or methyl in the presence of a lower-alkanol of the formula R$_1$OH. The compounds of formula I where Q is COOR' and R is hydrogen are also prepared by this procedure but substituting in place of PY—CH$_2$—C(=O)—R a molar equivalent quantity of α-PY-β-dimethylaminoacrolein of the formula (CH$_3$)$_2$N—CH=C(PY)—CHO.

The compounds of formula I where Q is cyano are prepared from the corresponding 2-chloro(or bromo) compound as noted above or by the generally known procedure of reacting said α-PY-β-dimethylaminoacrolein with malononitrile in the presence of an alkali metal salt of a lower-alkanol and said lower-alkanol (R$_1$OH), this reaction having been specifically shown by said Nantka-Namirski et al., Pol. J. Pharmacol. Pharm. 30, 707 (1978), in the preparation of 3-cyano-2-methoxy-5-(4-pyridinyl)pyridine.

The following examples will further illustrate the invention without, however, limiting it thereto.

1. 2-Methoxy-6-methyl-5-(4-pyridinyl)pyridine, alternatively named 6-methoxy-2-methyl-[3,4'-bipyridine]—A mixture containing 21 g of 2-chloro-6-methyl-5-(4-pyridinyl)pyridine, 27 g of sodium methoxide and 300 ml of methanol was refluxed for about 113 hours and the reaction mixture was then heated in vacuo to distill off the solvent. The residue was taken up in 300 ml of water, the solution treated with decolorizing charcoal, the mixture filtered and the filtrate cooled whereupon there separated an oil which solidified on standing. The solid was collected, dried in a vacuum oven at room temperature to yield 14 g of 2-methoxy-6-methyl-5-(4-pyridinyl)pyridine, m.p. 85°–90° C.

Acid-addition salts of 2-methoxy-6-methyl-5-(4-pyridinyl)pyridine are conveniently prepared by adding to a mixture of 2 g of 2-methoxy-6-methyl-5-(4-pyridinyl)pyridine in about 40 ml of anhydrous methanol a slight molar equivalent excess of the appropriate acid, e.g., methanesulfonic acid, concentrated sulfuric acid, concentrated phosphoric acid, lactic acid, to a pH of about 2–3, chilling the mixture after partial evaporation and collecting the precipitated salt, e.g., dimethanesulfonate, sulfate, phosphate, lactate, respectively.

2. 3-Bromo-2-methoxy-5-(4-pyridinyl)pyridine, alternatively named 5-bromo-6-methoxy-[3,4'-bipyridine]—A mixture containing 14 g of 3-bromo-2-chloro-5-(4-pyridinyl)pyridine, 10.8 g of sodium methoxide and 150 ml of methanol was refluxed with stirring for three hours and filtered while hot. The filtrate was diluted with water and cooled. The product that separated was collected, washed with water, dried, recrystallized from cyclohexane using decolorizing charcoal, washed with n-hexane and dried in vacuo at 60° C. to produce 9.5 g of 3-bromo-2-methoxy-5-(4-pyridinyl)pyridine, m.p. 136°–138° C.

Acid-addition salts of 3-bromo-2-methoxy-5-(4-pyridinyl)pyridine are conveniently prepared by adding to a mixture of 2 g of 3-bromo-2-methoxy-5-(4-pyridinyl)pyridine in about 40 ml of anhydrous methanol a slight molar equivalent excess of the appropriate acid, e.g., methanesulfonic acid, concentrated sulfuric acid, concentrated phosphoric acid, lactic acid, to a pH of about 2–3, chilling the mixture after partial evaporation and collecting the precipitated salt, e.g., dimethanesulfonate, sulfate, phosphate, lactate, respectively.

3. Methyl 2-Methoxy-6-methyl-5-(4-pyridinyl)pyridine-3-carboxylate, alternatively named methyl 6-methoxy-2-methyl-[3,4'-bipyridine]-3-carboxylate—A mixture containing 15 g of 1-(4-pyridinyl)propan-2-one, 15.5 g of methyl ethoxymethylenecyanoacetate and 250 ml of methanol was refluxed with stirring for 3 and ½ hours and the reaction mixture was cooled to room temperature. A red solid (impurities) was filtered off and the filtrate was concentrated in vacuo to remove the solvent. The residue was chromatographed on 300 g of silica gel using 5% methanol in ether as the eluant. The solid obtained after evaporation of the eluant was recrystallized once from ether-methanol and once from cyclohexane-ether to produce 5.2 g of methyl 2-methoxy-6-methyl-5-(4-pyridinyl)pyridine-3-carboxylate, 136°–138° C..

Acid-addition salts of methyl 2-methoxy-6-methyl-5-(4-pyridinyl)pyridine-3-carboxylate are conveniently prepared by adding to a mixture of 2 g of methyl 2-methoxy-6-methyl-5-(4-pyridinyl)pyridine-3-carboxylate in about 40 ml of anhydrous methanol a slight molar equivalent excess of the appropriate acid, e.g., methanesulfonic acid, concentrated sulfuric acid, concentrated phosphoric acid, lactic acid, to a pH of about 2–3 chilling the mixture after partial evaporation and collecting the precipitated salt, e.g., dimethanesulfonate, sulfate, phosphate, lactate, respectively.

4. 3-Cyano-2-methoxy-5-(4-pyridinyl)pyridine, a known compound, alternatively named 6-methoxy-[3,4'-bipyridine]-5-carbonitrile, m.p. 213°–215° C. with decomposition, 3.6 g, was prepared following the procedure described in Example 2 using 7.2 g of 2-chloro-3-cyano-5-(4-pyridinyl)pyridine, 2.0 g of sodium methoxide and 150 ml of methanol, a heating period of three hours, and recrystallizations once from methanol and once from dimethylformamide using decolorizing charcoal, washing with ether and drying in a vacuum oven at 75°–80° C.

The intermediate 2-chloro-3-cyano-5-(4-pyridinyl)pyridine, m.p. 219°–223° C. with decomposition, 126.2 g, was obtained following the procedure described by Nantka-Namirski et al., supra, using 189.4 g of 3-cyano-5-(4-pyridinyl)pyridine, 120 ml of phosphorus oxychloride, 3.5 ml of dimethylformamide and a refluxing period of 8 and ½ hours.

2-Methoxy-3-cyano-5-(4-pyridinyl)pyridine also can be prepared by the procedure described by Nantka-Namirski et al., supra, by reacting 3-dimethylamino-2-(4-pyridinyl)acrolein with malononitrile and sodium methoxide in methanol.

Following the procedure described in Example 2 but using in place of 3-bromo-2-chloro-5-(4-pyridinyl)pyridine, methanol and sodium methoxide corresponding molar equivalent quantities of 2-bromo(or chloro)-3-Q-5-PY-6-R-pyridine, either methanol or ethanol and either an alkali metal methoxide or ethoxide, respectively, it is contemplated that the corresponding 2-methoxy(or ethoxy)-3-Q-5-PY-6-R-pyridines of examples 5 through 22 can be obtained.

5. 2-Ethoxy-5-(4-pyridinyl)pyridine, using 2-bromo-5-(4-pyridinyl)pyridine, ethanol and sodium ethoxide.

6. 2-Methoxy-5-(3-pyridinyl)pyridine, using 2-chloro-3-(3-pyridinyl)pyridine, methanol and potassium methoxide.

7. 5-(3-Ethyl-4-pyridinyl)-2-methoxypyridine, using 2-chloro-5-(3-ethyl-4-pyridinyl)pyridine, methanol and sodium methoxide.

8. 2-Methoxy-6-methyl-5-(4-pyridinyl)pyridine, using 2-chloro-6-methyl-5-(4-pyridinyl)pyridine, methanol and sodium methoxide.

9. 2-Ethoxy-6-ethyl-5-(4-pyridinyl)pyridine, using 2-chloro-6-ethyl-5-(4-pyridinyl)pyridine, ethanol and sodium ethoxide.

10. 2-Methoxy-6-n-propyl-5-(4-pyridinyl)pyridine, using 2-chloro-6-n-propyl-5-(4-pyridinyl)pyridine, methanol and sodium methoxide.

11. 6-n-Butyl-2-methoxy-5-(4-pyridinyl)pyridine, using 6-n-butyl-2-chloro-5-(4-pyridinyl)pyridine, methanol and sodium methoxide.

12. 6-Ethyl-2-methoxy-5-(2-methyl-4-pyridinyl)pyridine, using 2-chloro-6-ethyl-5-(2-methyl-4-pyridinyl)pyridine, methanol and sodium methoxide.

13. 6-Ethyl-2-methoxy-5-(3-pyridinyl)pyridine, using 2-chloro-6-ethyl-5-(3-pyridinyl)pyridine, methanol and sodium methoxide.

14. 3-Chloro-2-methoxy-6-methyl-5-(4-pyridinyl)pyridine, using 2,3-dichloro-6-methyl-5-(4-pyridinyl)pyridine, methanol and sodium methoxide.

15. 3-Chloro-2-methoxy-6-methyl-5-(3-pyridinyl)pyridine, using 2,3-dichloro-6-methyl-5-(3-pyridinyl)pyridine, methanol and sodium methoxide.

16. 3-Chloro-6-methyl-2-methoxy-5-(2-methyl-4-pyridinyl)pyridine, using 2,3-dichloro-6-ethyl-5-(2-methyl-4-pyridinyl)pyridine, methanol and sodium methoxide.

17. 3-Bromo-2-methoxy-6-methyl-5-(4-pyridinyl)pyridine, using 3-bromo-2-chloro-6-methyl-5-(4-pyridinyl)pyridine, methanol and sodium methoxide.

18. 3-Chloro-2-ethoxy-6-ethyl-5-(4-pyridinyl)pyridine, using 2,3-dichloro-6-ethyl-5-(4-pyridinyl)pyridine, ethanol and sodium ethoxide.

19. 3-Bromo-6-isopropyl-2-methoxy-5-(4-pyridinyl)pyridine, using 3-bromo-2-chloro-6-isopropyl-5-(4-pyridinyl)pyridine, methanol and sodium methoxide.

20. 3-Chloro-2-methoxy-6-methyl-5-(2,6-dimethyl-4-pyridinyl)pyridine, using 2,3-dichloro-6-methyl-5-(2,6-dimethyl-4-pyridinyl)pyridine, methanol and sodium methoxide.

21. 3-Cyano-2-methoxy-5-(3-pyridinyl)pyridine, using 2-chloro-3-cyano-5-(3-pyridinyl)pyridine, methanol and sodium methoxide.

22. 2-Ethoxy-3-cyano-5-(2-methyl-4-pyridinyl)pyridine, using 2-chloro-3-cyano-5-(2-methyl-4-pyridinyl)pyridine, ethanol and sodium ethoxide.

Following the procedure described in Example 3 but using in place of 1-(4-pyridinyl)-2-propanone, methyl ethoxymethylenecyanoacetate and methanol corresponding molar equivalent quantities of 1-PY-2-alkanone or β-dimethylamino-α-PY-acrolein, lower-alkyl ethoxymethylenecyanoacetate and lower-alkanol respectively, it is contemplated that the corresponding lower-alkyl 2-methoxy(or ethoxy)-5-PY-6-R-pyridines of Examples 23-27 can be obtained.

23. Ethyl 2-Ethoxy-6-ethyl-5-(4-pyridinyl)pyridine-3-carboxylate, using 1-(4-pyridinyl)-2-butanone, ethyl ethoxymethyleneeyanoacetate and ethanol.

24. Methyl 2-Methoxy-6-n-propyl-5-(3-pyridinyl)pyridine-3-carböxylate, using 1-(3-pyridinyl)-2-pentanone, methyl ethoxymethylenecyanoacetate and methanol.

25. Methyl 2-Methoxy-6-methyl-5-(2-methyl-4-pyridinyl)pyridine-3-carboxylate, using 1-(2-methyl-4- pyridinyl)-2-propanone, methyl ethoxymethylenecyanoacetate and methanol.

26. Methyl 2-Methoxy-5-(4-pyridinyl)pyridine-3-carboxylate, using β-dimethylamino-α-(4-pyridinyl)acrolein, methyl ethoxymethylenecyanoacetate and methanol.

27. Ethyl 2-Ethoxy-5-(3-pyridinyl)pyridine-3-carboxylate, using β-dimethylamino-α-(3-pyridinyl)acrolein, ethyl ethoxymethylenecyanoacetate and ethanol.

The usefulness of the compounds of formula I, or pharmaceutically acceptable acid-addition salts thereof, as cardiotonic agents is demonstrated by their effectiveness in standard pharmacological test procedures, for example, in causing a significant increase in the contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the isolated cat or guinea pig atria and papillary muscle procedure, the compounds of formula I or pharmaceutically acceptable acid-addition salts thereof at doses of 10, 30 and/or 100 μg/ml., were found to cause significant increases, that is, greater than 25% (cat) or 30% (guinea pig) in papillary muscle force and significant increases, that is, greater than 25% (cat) or 30% (guinea pig), in right atrial force, while causing a lower percentage increase in right atrail rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested at said dose levels by this procedure in the cat, the compound of Example 2, namely 3-bromo-2-methoxy-5-(4-pyridinyl)pyridine, was found to cause respective increases in papillary muscle force and right atrial force of 48% and 28% at 10 μg/ml. and 78% and 51% at 30 μg/ml. When tested by this procedure in the guinea pig, the compound of Example 1, namely 2-methoxy-6-methyl-5-(4-pyridinyl)pyridine was found to cause respective increases in papillary muscle force and right atrial force of 36% and 15% at 10 μg/ml, 110% and 23% at 30 μg/ml and 273% and 116% at 100 μg/ml; the compound of Example 3, methyl 2-methoxy-6-methyl-5-(4-pyridinyl)-pyridine-3-carboxylate, was found to cause respective increases in papillary muscle force and right atrial force of 48% and 34% at 10 μg/ml, 54% and 38% at 30 μg/ml and 95% and 103% at 100 μg/ml; and, the compound of Example 4, namely 3-cyano-2-methoxy-5-(4-pyridinyl)pyridine, was found to cause respective increases in papillary muscle force and right atrail force of 109% and 68% at 30 μg/ml and 78% and 97% at 100 μg/ml.

The present invention includes within its scope a cardiotonic composition for increasing cardiac contractility, said composition comprising a pharmaceutically acceptable carrier and, as the active component thereof, a cardiotonically effective amount of the compound of formula I or said salt thereof. The invention also includes within its scope the method for increasing cardiac contractility in a patient requiring such treatment which comprises administering to such patient said cardiotonic composition providing a cardiotonically effective amount of the compound of formula I or the compound of formula I where Q is cyano only when R is hydrogen or said salt thereof. In clinical practice said compound will normally be administered orally or parenterally in a wide variety of dosage forms.

Solid compositions for oral admininstration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such a magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 2-($R_1$O)-3-Q-5-PY-6-R-pyridine having the formula

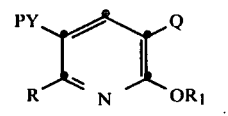

or a pharmaceutically acceptable acid-addition salt thereof, where $R_1$ is methyl or ethyl, R is hydrogen or lower-alkyl, Q is hydrogen, bromo, chloro or COOR′ where R' is lower-alkyl, and PY is 4(or 3)-pyridinyl or 4(or 3)-pyridinyl having one or two lower-alkyl substituents.

2. A compound according to claim 1 where $R_1$ is methyl, Q is hydrogen, R is methyl or ethyl, and PY is 4(or 3)-pyridinyl.

3. 2-Methoxy-6-methyl-5-(4-pyridinyl)pyridine according to claim 1.

4. A cardiotonic composition for increasing cardiac contracility, said composition comprising a pharmaceutically acceptable carrier and, as the active component thereof, a cardiotonically effective amount of 2-($R_1$O)-3-Q-5-PY-6-R-pyridine or pharmaceutically acceptable acid-addition salt thereof, where $R_1$ is methyl or ethyl, R is hydrogen or lower-alkyl, Q is hydrogen, bromo, chloro or COOR' where R' is lower-alkyl, and PY is 4(or 3)-pyridinyl or 4(or 3)-pyridinyl having one or two lower-alkyl substituents.

5. A composition according to claim 4 where $R_1$ is methyl, Q is hydrogen, PY is 4(or 3)-pyridinyl and R is methyl or ethyl.

6. A composition according to claim 4 where the active component is 2-methoxy-6-methyl-5-(4-pyridinyl)pyridine.

7. The method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of 2-($R_1$O)-3-Q-5-PY-6-R-pyridine or pharmaceutically acceptable acid-addition salt thereof, where $R_1$ is methyl or ethyl, R is hydrogen or lower-alkyl, Q is hydrogen, bromo, chloro or COOR' where R' is lower-alkyl, and PY is 4(or 3)-pyridinyl or 4(or 3)-pyridinyl having one or two lower-alkyl substituents or where Q is cyano only when R is hydrogen.

8. The method according to claim 7 where $R_1$ is methyl, Q is hydrogen, R is methyl or ethyl.

9. The method according to claim 7 where the active component is 2-methoxy-6-methyl-5-(4-pyridinyl)pyridine.

* * * * *